US012605164B2

(12) United States Patent
Liou et al.

(10) Patent No.: US 12,605,164 B2
(45) Date of Patent: Apr. 21, 2026

(54) TACTICAL HEMOSTATIC BANDAGE

(71) Applicants: SOLID YEAR CO., LTD., New Taipei City (TW); TAICEND TECHNOLOGY CO., LTD., Kaohsiung City (TW)

(72) Inventors: Yu-Ren Liou, New Taipei City (TW); Chao-Hsin Lin, New Taipei City (TW); Chuan-Shih Wu, New Taipei City (TW); Gou-Don Chu, New Taipei City (TW)

(73) Assignees: SOLID YEAR CO., LTD., New Taipei City (TW); TAICEND TECHNOLOGY CO., LTD., Kaohsiung City (TW)

( * ) Notice: Subject to any disclaimer, the term of this patent is extended or adjusted under 35 U.S.C. 154(b) by 114 days.

(21) Appl. No.: 18/434,360

(22) Filed: Feb. 6, 2024

(65) Prior Publication Data

US 2025/0204928 A1 Jun. 26, 2025

(30) Foreign Application Priority Data

Dec. 20, 2023 (TW) ................................. 112149843

(51) Int. Cl.
*A61B 17/132* (2006.01)
*A61B 17/12* (2006.01)
(Continued)

(52) U.S. Cl.
CPC .......... *A61B 17/1327* (2013.01); *A61F 13/01* (2024.01); *A61B 2017/12004* (2013.01); *A61F 2013/0028* (2013.01); *A61F 2013/422* (2013.01)

(58) Field of Classification Search
CPC ......... A61B 17/132–1327; A61F 13/01; A61F 13/0273; A61F 2013/00565; A44B 11/04;
(Continued)

(56) References Cited

U.S. PATENT DOCUMENTS 2,095,340 A * 10/1937 Meyer .................... A44B 11/04
2/268
2,212,862 A * 8/1940 Hirsh ..................... A44B 11/04
24/336
(Continued)

*Primary Examiner* — Brigid K Byrd
(74) *Attorney, Agent, or Firm* — Birch, Stewart, Kolasch & Birch, LLP

(57) ABSTRACT

A pressurized tourniquet includes an elastic band, a hemostatic dressing, and a pressurized member. A through tough is formed at the outer surface of the elastic band and has an extending direction vertical to the longitudinal direction of the elastic band and parallel to the width direction of the elastic band. The hemostatic dressing is disposed to the inner surface of the elastic band. The pressurized member has a base portion, an insertion portion connected with the base portion and detachably inserted in the through tough and having one end forming an anchor portion protruding from and interfered with the through tough, and a pressurized portion connected with the base portion and parallel to the insertion portion to form a slot therebetween for passage of the elastic band. Thus, the pressurized tourniquet of the present invention has advantages of convenient manufacturing and easy replacement of accessories.

7 Claims, 13 Drawing Sheets

(51) Int. Cl.
    *A61F 13/00*       (2024.01)
    *A61F 13/01*       (2024.01)
    *A61F 13/42*       (2006.01)

(58) Field of Classification Search
    CPC ........ A61M 5/1418; A61M 2025/0206; A61M
                                      2025/024
    See application file for complete search history.

(56)                   References Cited

U.S. PATENT DOCUMENTS

| | | | |
|---|---|---|---|
| 10,765,437 B1 * | 9/2020 | Antonio ............. | A61B 17/1325 |
| 2007/0185428 A1 * | 8/2007 | Harder ............... | A61B 17/1322 |
| | | | 602/75 |
| 2010/0057120 A1 * | 3/2010 | Kirkham ............ | A61B 17/1322 |
| | | | 606/203 |
| 2016/0128700 A1 * | 5/2016 | Fry .................... | A61B 17/1322 |
| | | | 606/203 |
| 2020/0187958 A1 * | 6/2020 | Bagby ................ | A61B 17/1325 |
| 2021/0346035 A1 * | 11/2021 | Wagner ............. | A61B 17/1322 |
| 2024/0307233 A1 * | 9/2024 | Naimer .............. | A61F 13/0203 |

* cited by examiner

TACTICAL HEMOSTATIC BANDAGE

BACKGROUND OF THE INVENTION

1. Field of the Invention

The present invention relates to pressurized tourniquets and more particularly, to a pressurized tourniquet that can simplify its production process.

2. Description of the Related Art

When a person has a large or deep wound, in addition to treating the wound, a tourniquet is commonly used to stop bleeding. To put it simply, a tourniquet mainly uses an elastic band to wrap around the injured limb together with a pressurized member. After wrapping, the pressurized member applies appropriate pressure to the wound for achieving a hemostatic effect.

However, in a traditional tourniquet, the pressurized member is sewn directly onto one side of the elastic band during manufacturing. This makes the production process more time-consuming. Once the elastic band is too dirty, the hemostatic dressing needs to be replaced or the pressurized member is damaged, the user needs to purchase a new tourniquet. It is impossible for the user to simply replace the elastic band, the hemostatic dressing or the pressurized member with a new one. This results in an added financial burden for the user.

SUMMARY OF THE INVENTION

It is one objective of the present invention to provide a pressurized tourniquet, which can simplify production process and replace damaged accessories.

To attain the above objective, the pressurized tourniquet of the present invention comprises an elastic band, a hemostatic dressing, and a pressurized member. The elastic band includes an inner surface, an outer surface, and a through tough formed at the outer surface and having an extending direction vertical to a longitudinal direction of the elastic band and parallel to a width direction of the elastic band. The hemostatic dressing is disposed to the inner surface of the elastic band for absorbing blood and secretions from wounds. The pressurized member includes a base portion, an insertion portion, and a first pressurized portion. The insertion portion and the first pressurized portion are on the same side of the base portion and each have one end thereof connected with the base portion. The insertion portion is detachably inserted in the through tough of the elastic band and has a free end forming an anchor portion protruding from one end of the through tough and interfered with the through tough. The first pressurized portion and the insertion portion are parallel to and spaced from each other to form a first slot therebetween for passage of the elastic band.

It can be seen from the above that the pressurized member provided by the pressurized tourniquet of the present invention is detachably assembled with the elastic band and not fixed to each other by traditional sewing methods. This makes the production process relatively simple and fast. Once the elastic band is too dirty, the hemostatic dressing needs to be replaced, or the pressurized member is damaged, the user simply replaces the damaged accessories without the need to discard the entire set. This can significantly reduce the financial burden for the user.

Preferably, a free end of the first pressurized portion forms a first limiting hook in the direction of the anchor portion. A first opening communicating with the first slot is formed between the first limiting hook and the anchor portion. In this way, the first opening allows the elastic band to easily enter and exit the first slot, and the first limiting hook limits the elastic band in the first slot.

Preferably, the pressurized member further includes a second pressurized portion. The second pressurized portion and the first pressurized portion are on the same side of the base portion and each have one end thereof connected with the base portion. The second pressurized portion and the insertion portion are parallel to and spaced from each other to form a second slot therebetween for passage of the elastic band.

Preferably, a free end of the second pressurized portion forms a second limiting hook in the direction of the anchor portion. A second opening communicating with the second slot is formed between the second limiting hook and the anchor portion. In this way, the second opening allows the elastic band to easily enter and exit the second slot, and the second limiting hook limits the elastic band in the second slot.

Preferably, the first pressurized portion has a first inclined surface abutted with the first limiting hook. In this way, the first inclined surface makes it easier for the elastic band to hook with the first limiting hook and makes it difficult for the elastic band to escape from the first slot through the first opening.

Preferably, the elastic band includes a bandage provided with the inner surface and the outer surface, and a positioning cloth having two opposite sides thereof sewn to the bandage, such that the through trough is formed between the bandage and the positioning cloth. The anchor portion has two ends thereof engaged with the two opposite sides of the positioning cloth, such that pressurized member cannot be easily escaped from the through trough.

Preferably, a dressing change indicator label is disposed between the bandage and the hemostatic dressing. Through the dressing replacement indicator label, the user can assess whether the wound exudate or blood exceeds the absorbent capacity of the hemostatic dressing. This facilitates determining the opportune moment to replace the hemostatic dressing.

Preferably, a bandage fastener is inserted into a tail groove formed by folding one end of the elastic band inwards and sewing it together. In this way, after the bandage is wrapped around an affected limb, the bandage is fixed through the bandage fastener.

Preferably, the elastic band is a bandage. One end of the bandage is folded back and fixed by sewing to form an inner layer and an outer layer stacked on the inner layer. The outer layer has a positioning portion provided with two opposite sides thereof sewn to the inner layer, such that the through trough is formed between the positioning portion and the inner layer. The anchor portion has two ends thereof engaged with the two opposite sides of the positioning portion, such that pressurized member cannot be easily escaped from the through trough.

Preferably, a dressing change indicator label is disposed between the inner layer and the hemostatic dressing. The positioning portion of the outer layer further has a notch abutted with one end of the through trough and corresponding to the dressing change indicator label. Through the dressing replacement indicator label, the user can assess whether the wound exudate or blood exceeds the absorbent capacity of the hemostatic dressing.

Preferably, a bandage fastener is detachably installed in a tail groove formed by folding the other end of the elastic band inwards and fixing it by sewing. In this way, when the elastic band is wrapped around the affected limb, the elastic band is fixed by the bandage fastener.

Other advantages and features of the present invention will be fully understood by reference to the following specification in conjunction with the accompanying drawings, in which like reference signs denote like components of structure.

DETAILED DESCRIPTION OF THE INVENTION

Figure 1:
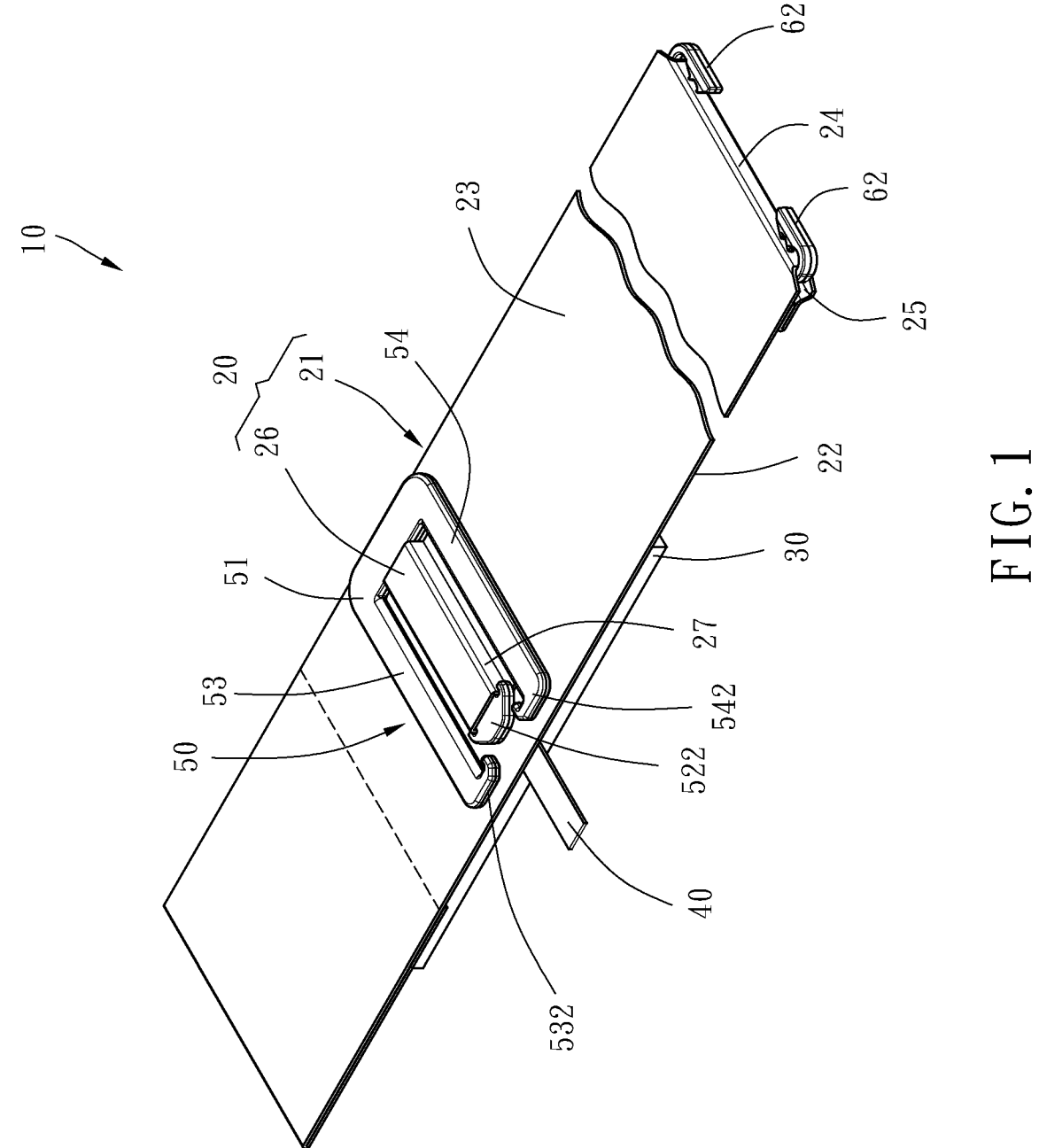
FIG. 1 is a perspective view of a pressurized tourniquet according to a first embodiment of the present invention.
Figure 2:
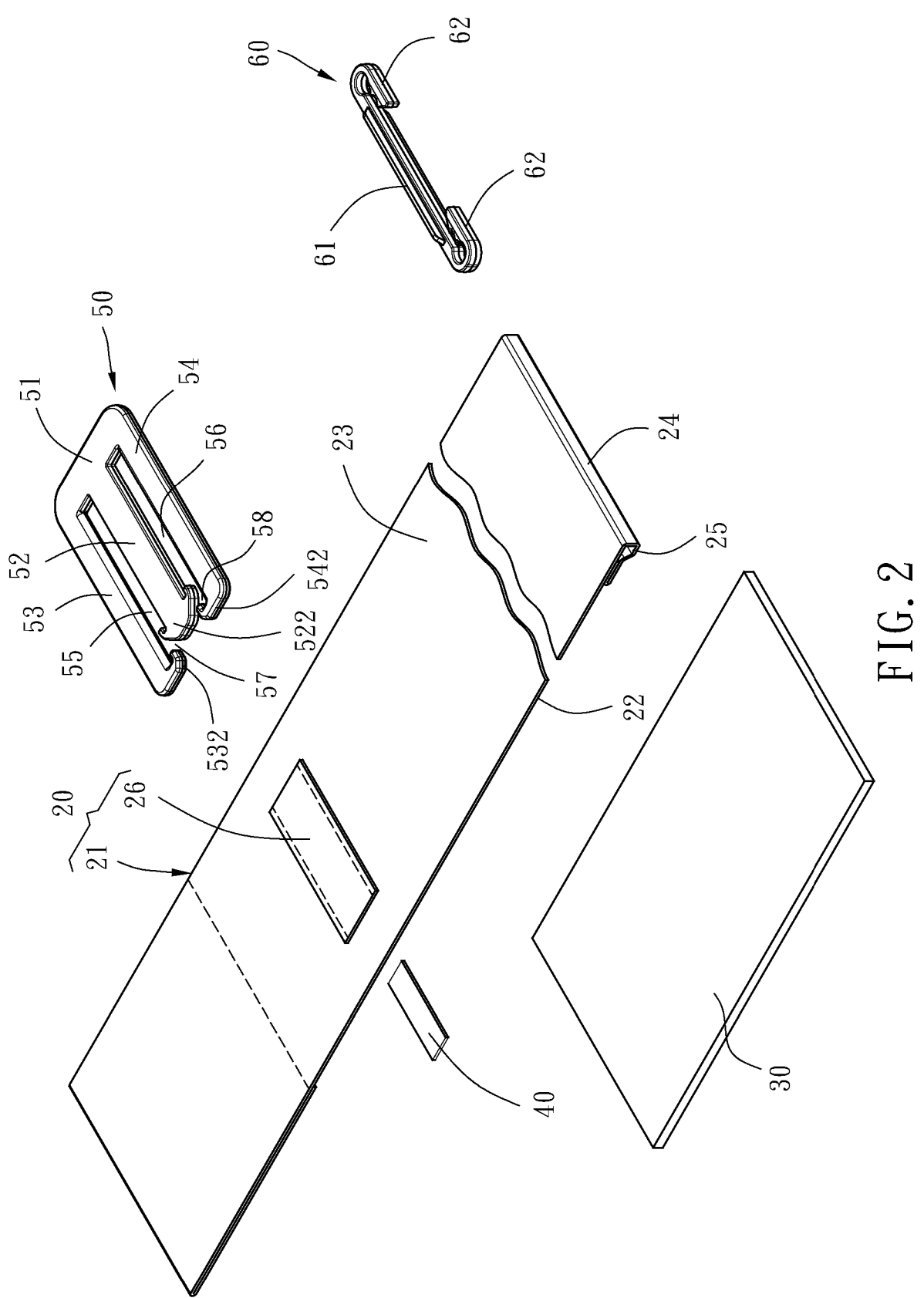
FIG. 2 is an exploded view of the pressurized tourniquet according to the first embodiment of the present invention.

Referring to FIGS. 1 and 2, a pressurized tourniquet 10 according to a first embodiment of the present invention comprises an elastic band 20, a hemostatic dressing 30, a dressing change indicator label 40, a pressurized member 50, and a bandage fastener 60.

Figure 4:
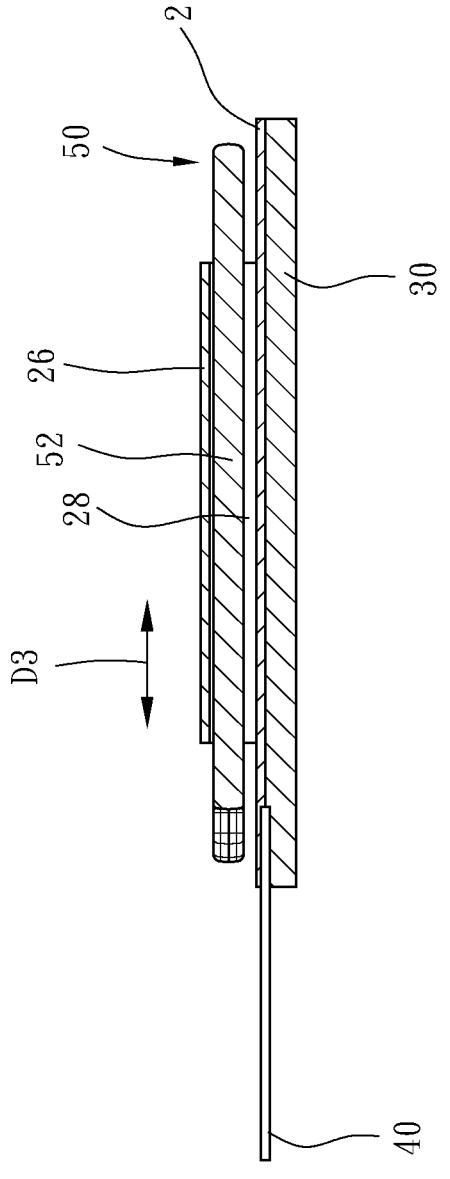
FIG. 4 is a sectional view taken along line 4-4 of FIG. 3.

The elastic band 20 includes a bandage 21 and a positioning cloth 26 in this embodiment. The bandage 21 has an inner surface 22 and an outer surface 23. A tail groove 25 is formed by folding one end of the bandage 21 inwards and sewing it together. Two opposite sides 27 of the positioning cloth 26 are sewn to the outer surface 23 of the bandage 21, such that a through trough 28 is formed between the bandage 21 and the positioning cloth 26, as shown in FIG. 4. An extending direction D3 of the through trough 28 is vertical to a longitudinal direction D1 of the bandage 21 and parallel to a width direction D2 of the bandage 21.

The hemostatic dressing 30 is attached to the inner surface 22 of the bandage 21 for absorbing blood and secretions from wounds.

The dressing change indicator label 40 has one end thereof disposed between the bandage 21 and the hemostatic dressing 30, and the other end thereof exposed outsides for the user to observe. The dressing replacement indicator label 40 is used to detect whether the exudate or blood from the wounds exceeds the absorption capacity of the hemostatic dressing 30, thereby facilitating determining the opportune moment to replace the hemostatic dressing 30.

Figure 3:
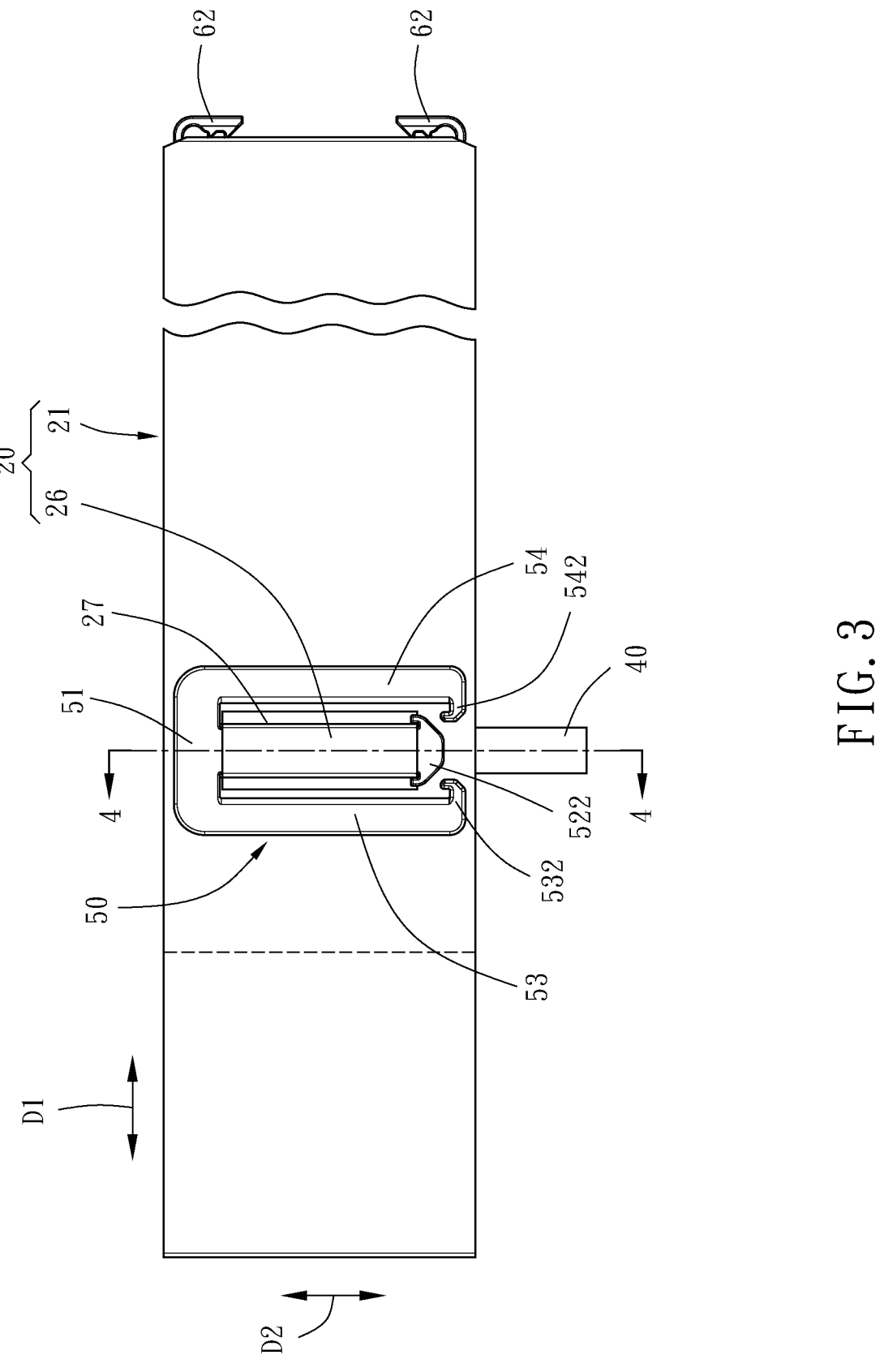
FIG. 3 is a top view of the pressurized tourniquet of the first embodiment according to the present invention.

The pressurized member 50 is made of plastic material. As shown in FIGS. 2 to 4, the pressurized member 50 includes a base portion 51, an insertion portion 52, a first pressurized portion 53, and a second pressurized portion 54. The insertion portion 52, the first pressurized portion 53, and the second pressurized portion 54 are on the same side of the base portion 51 and each have one end thereof connected with the base portion 51. The insertion portion 52, the first pressurized portion 53, and the second pressurized portion 54 are parallel to and spaced from each other, so that a first slot 55 is formed between the insertion portion 52 and the first pressurized portion 53, and a second slot 56 is formed between the insertion portion 52 and the second pressurized portion 54. In addition, a free end of the insertion portion 52 forms an anchor portion 522. The length of the first pressurized portion 53 is larger than the length of the insertion portion 52, and a free end of the first pressurized portion 53 forms a first limiting hook 532 in the direction of the anchor portion 522. A first opening 57 communicating with the first slot 55 is formed between the first limiting hook 532 and the anchor portion 522. Further, the length of the second pressurized portion 54 is larger than the length of the insertion portion 52, and a free end of the second pressurized portion 54 forms a second limiting hook 542 in the direction of the anchor portion 522. A second opening 58 communicating with the second slot 56 is formed between the second limiting hook 542 and the anchor portion 522. When used with the elastic band 20, as shown in FIGS. 1 to 4, the pressurized member 50 uses the insertion portion 52 to insert in the through trough 28 from one end of the positioning cloth 26 until the anchor portion 522 protrudes from the through groove 28 and hooks with the two opposite sides 27 of the positioning cloth 26, so that the anchor portion 522 and the positioning cloth 26 are interfered with each other. This prevents the insertion portion 52 from being easily separated from the through trough 28.

The bandage fastener 60 is made of plastic material. As shown in FIGS. 1 to 3, the bandage fastener 60 has a connecting portion 61 and two fixing hook portions 62 connected with two ends of the connecting portion 61 and located at the same side of the connecting portion 61. When used with the elastic band 20, the connecting portion 61 of the bandage fastener 60 is located in the tail groove 25, and the two fixing hook portions 62 of the bandage fastener 60 protrude from two ends of the tail groove 25.

Figure 5A:
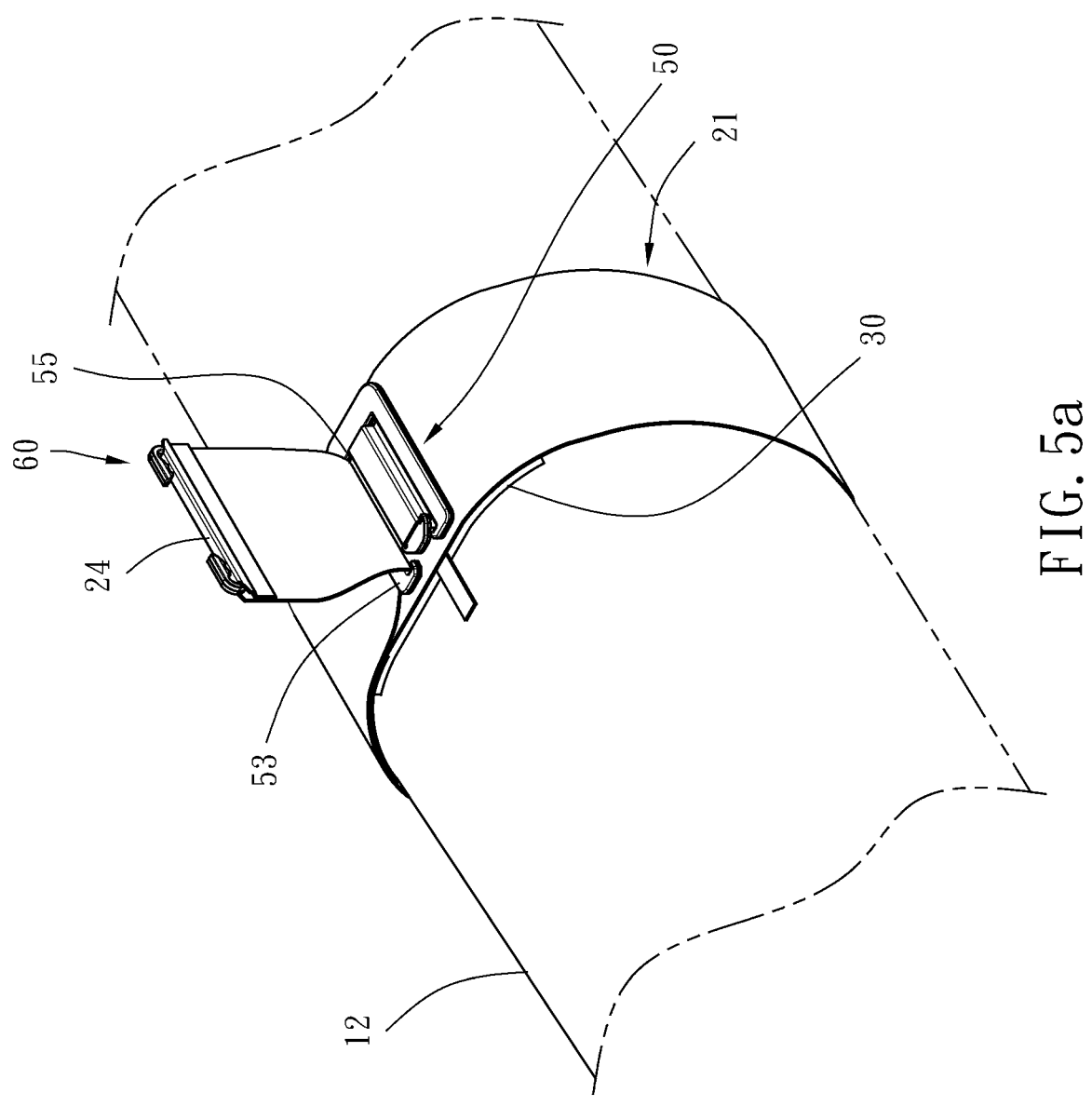
FIGS. 5a-5c is a flow chart for using the pressurized tourniquet according to the first embodiment of the present invention.
Figure 5B:
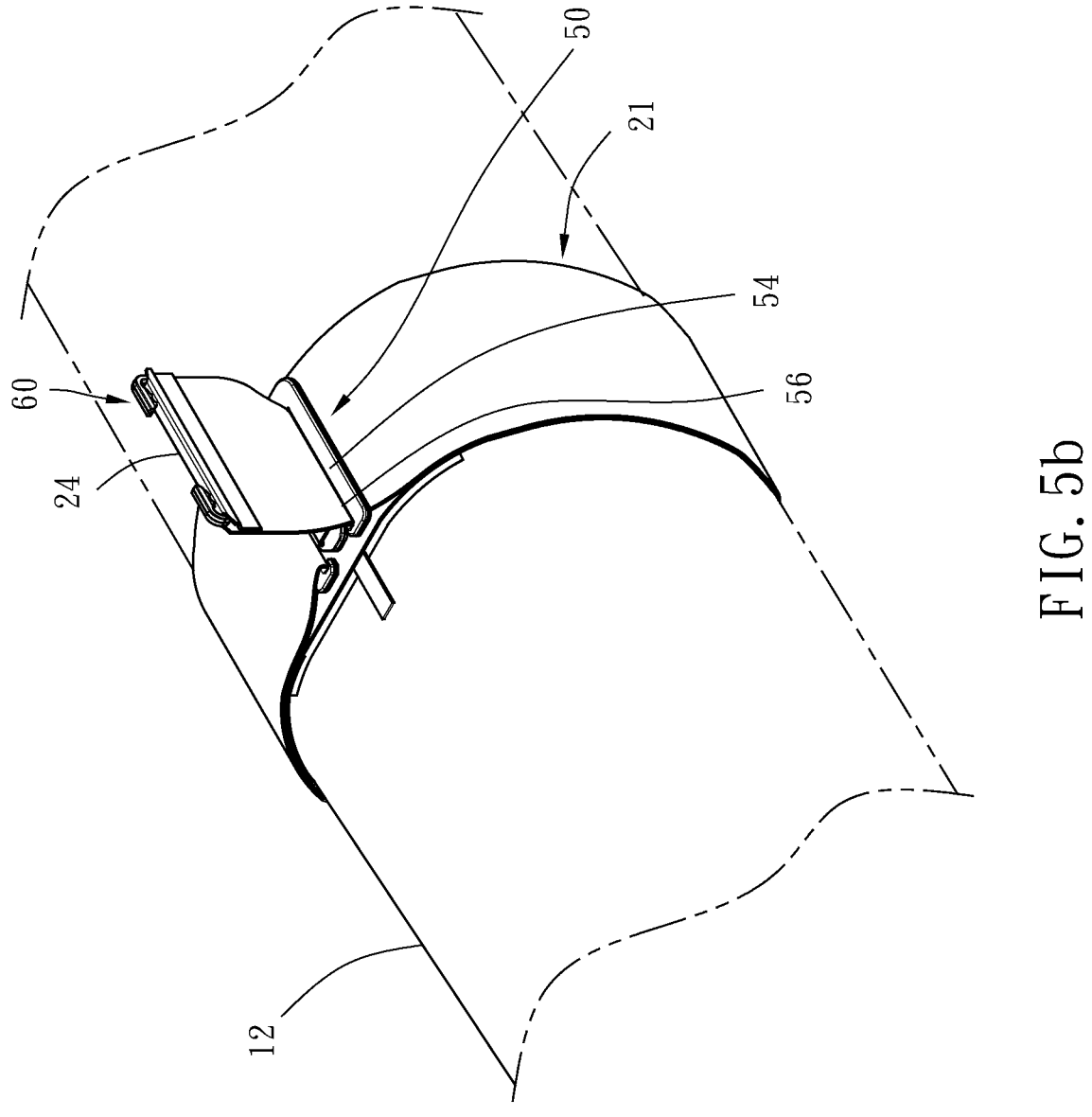
Figure 5C:
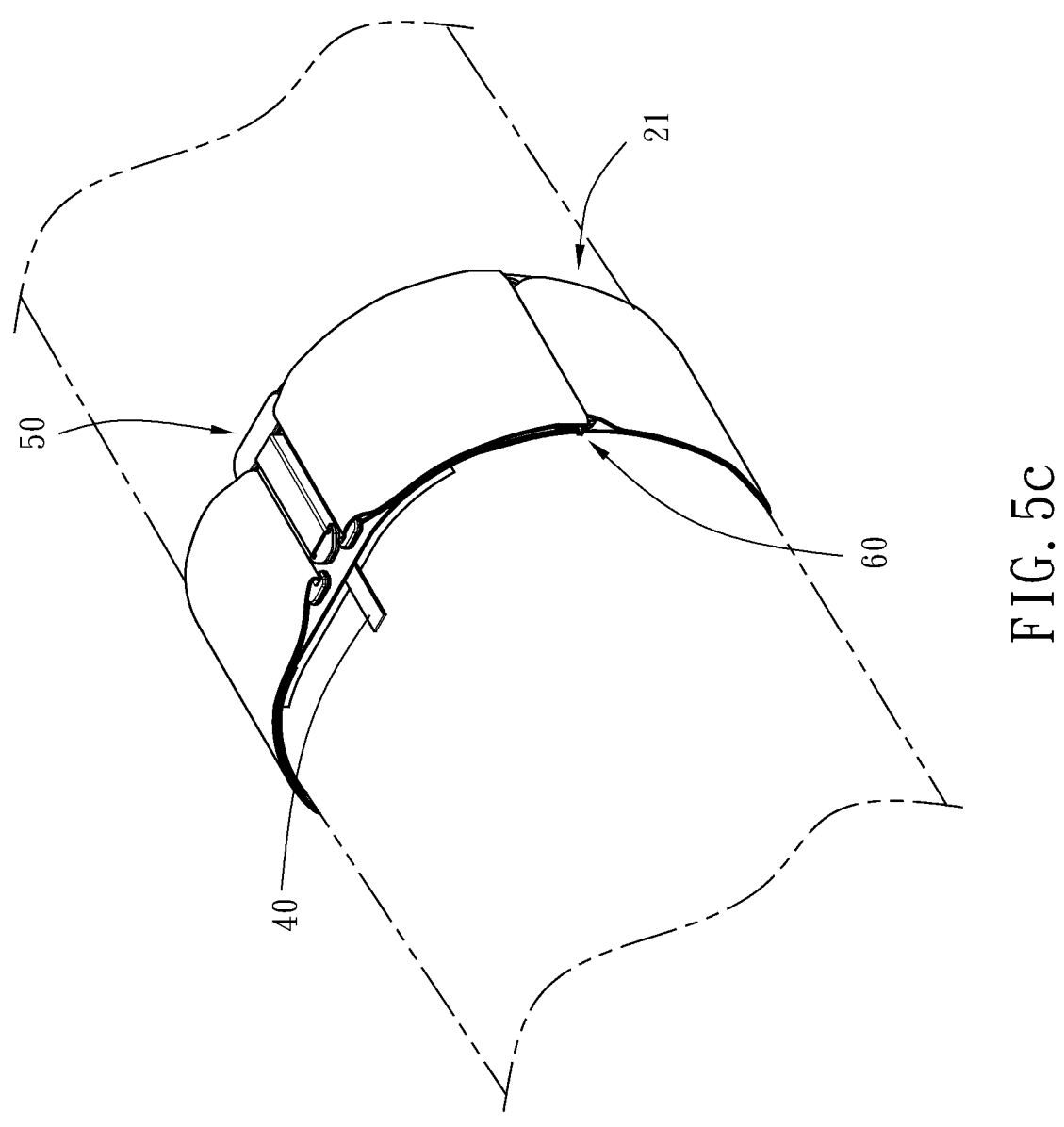

In actual use, as shown in FIGS. 5a to 5c, the hemostatic dressing 30 is first covered on the wound to absorb the blood and secretions from the wound, and then the bandage 21 is wrapped around the affected limb 12 and uses its one end 24 to pass through the first slot 55 together with the bandage fastener 60 from bottom to top. Thereafter, the bandage 21 is folded around the affected limb 12 uses its one end 24 to pass through the second slot 56 together with the bandage fastener 60 from bottom to top. Finally, the two fixing hook portions 62 of the bandage fastener 60 are used to directly fix one end 24 of the bandage 21 in an appropriate position, or one end 24 of the bandage 20 and the bandage fastener 60 can be wrapped several times to increase pressure. In this way, the bandage 21 can apply a certain degree of pressure on the wound through the first and second pressurized portions 53, 54 of the pressurized member 50 to achieve a hemostatic effect. In another usage situation, after the bandage fastener 60 passes through the second slot 56, the bandage 21 is continued to be wrapped around the affected limb 12 to cover the pressurized member 50. This can also apply a certain degree of pressure on the wound for achieving the hemostatic effect. Additionally, during the use of the pressurized tourniquet 10, the user can assess whether the bleeding amount of the wound exceeds the absorbent capacity of the hemostatic dressing 30 by checking the dressing change indicator label 40. Once the bleeding amount becomes excessive, the dressing change indicator label 40 will change color to remind the user that the hemostatic dressing 30 needs to be changed.

Figure 6:
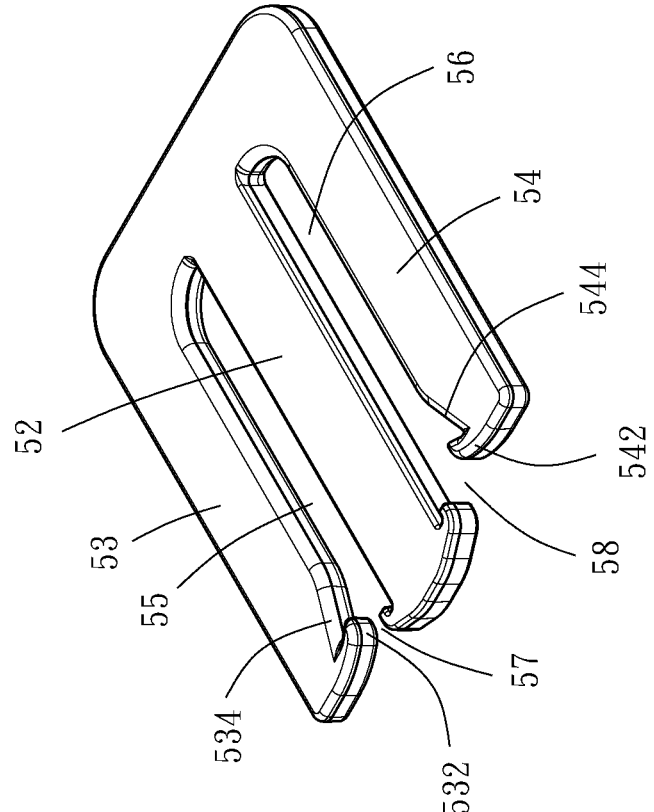
FIG. 6 is a perspective view of a pressurized member provided by the pressurized tourniquet according to a second embodiment of the present invention.
Figure 7:
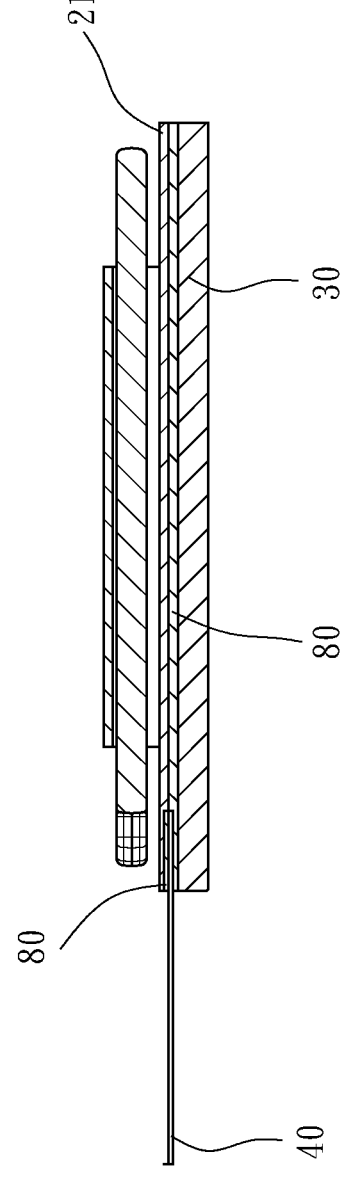
FIG. 7 is a sectional view of the pressurized tourniquet according to the second embodiment of the present invention.

What needs to be supplemented here is that the length of the first pressurized portion 53 and the length of the second pressurized portion 54 do not necessarily have to be greater than the length of the insertion portion 52. In the second embodiment of the present invention, as shown in FIG. 6, the length of the first pressurized portion 53 and the length of the second pressurized portion 54 can also be designed to be shorter than the length of the insertion portion 52 according to actual needs. In this way, the first and second pressurized portions 53, 54 of different lengths can be selected according to wounds of different sizes, so that the wounds of different sizes can obtain good pressurized effects. In addition, the first pressurized portion 53 further has a first inclined surface 534 adjacent to the first limiting hook 532, and the second pressurized portion 54 further has a second inclined surface 544 adjacent to the second limiting hook 542. Through the first and second inclined surfaces 534, 544, the elastic band 20 is relatively easy to be engaged with the first and second limiting hooks 532, 544, but relatively difficult to be separated from the first and second slots 55, 56 through the first and second openings 57, 58. As shown in FIG. 7, the hemostatic dressing 30 and the dressing change indicator label 40 can be adhered to the inner surface 23 of the elastic band 20 by using a back adhesive 80 for replacement purposes.

Figure 8:
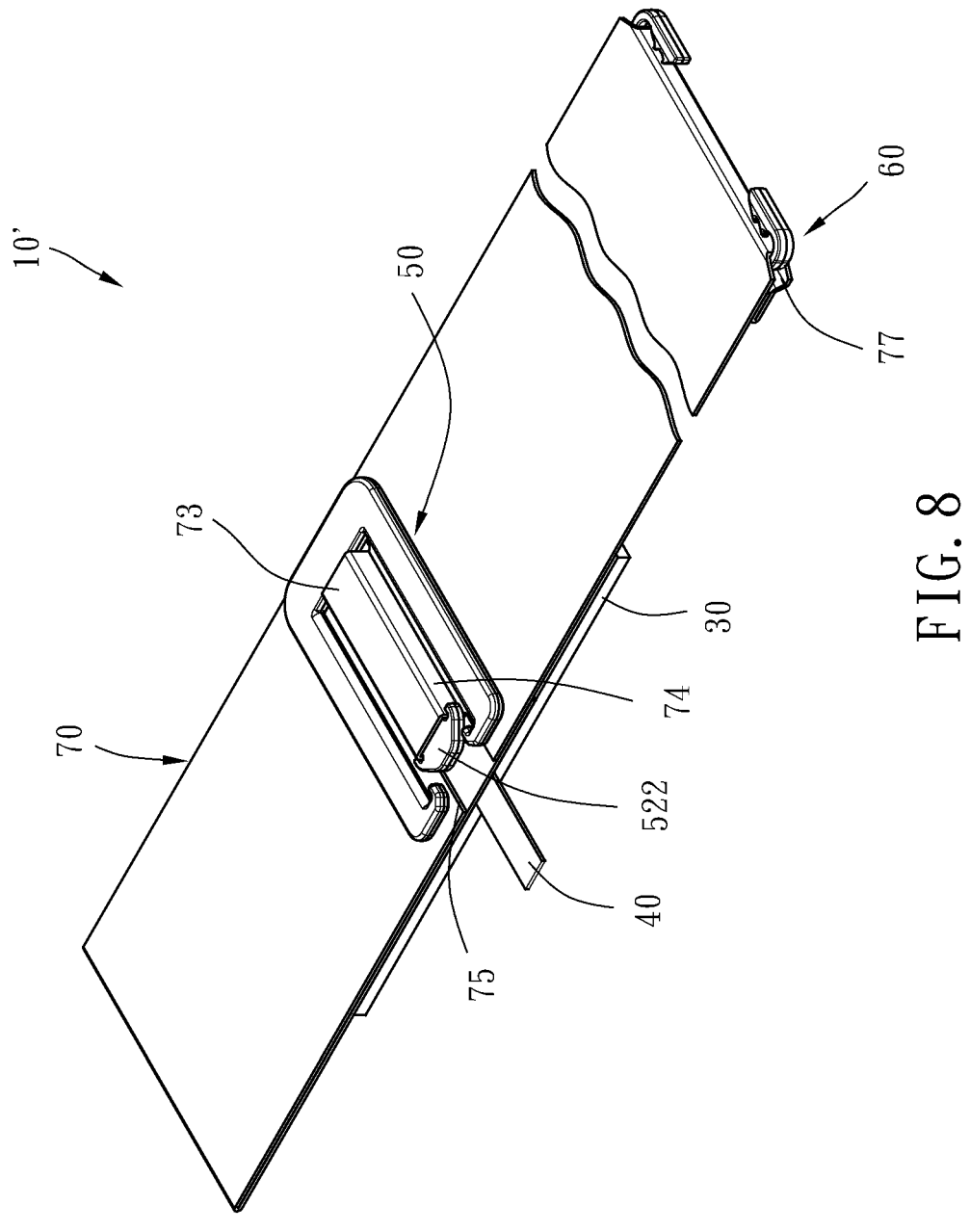
FIG. 8 is a perspective view of the pressurized tourniquet according to a third embodiment of the present invention.
Figure 9:
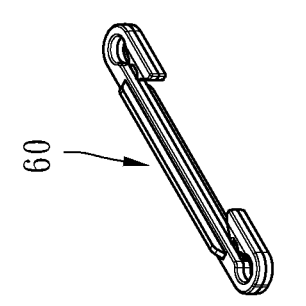
FIG. 9 is an exploded view of the pressurized tourniquet according to the third embodiment of the present invention.

As shown in FIGS. 8 and 9, the main structure of the pressurized tourniquet 10' provided by a third embodiment of the present invention is approximately the same with the first embodiment, but one of the differences therebetween lies in the structure of the elastic band 70. The structural configuration and overall usage method of the hemostatic dressing 30, the dressing change indicator label 40, the pressurized member 50 and the bandage fastener 60 are the same as those in the first embodiment, so they will not be described again hereunder.

Figure 10:
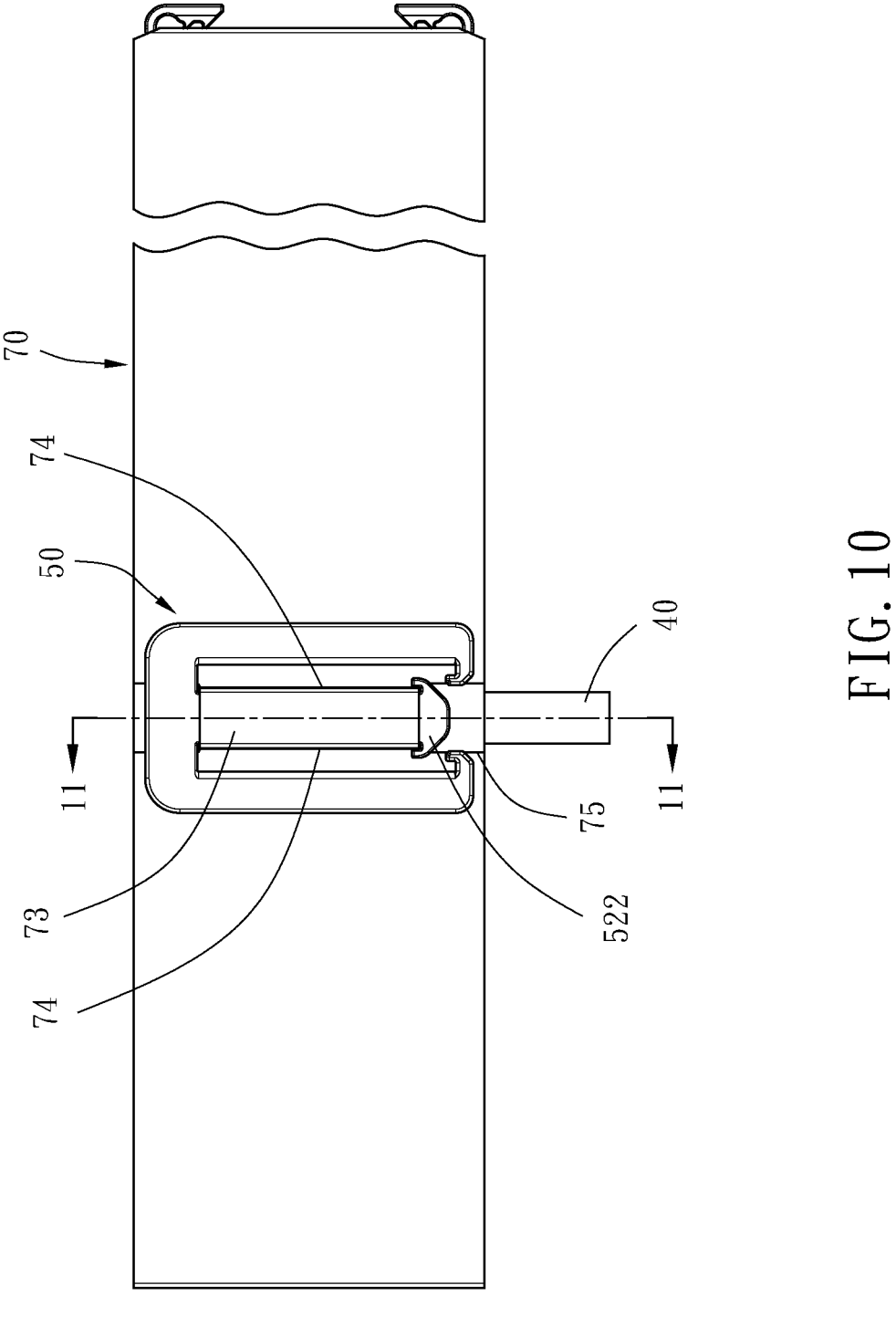
FIG. 10 is a top view of the pressurized tourniquet according to the third embodiment of the present invention.
Figure 11:
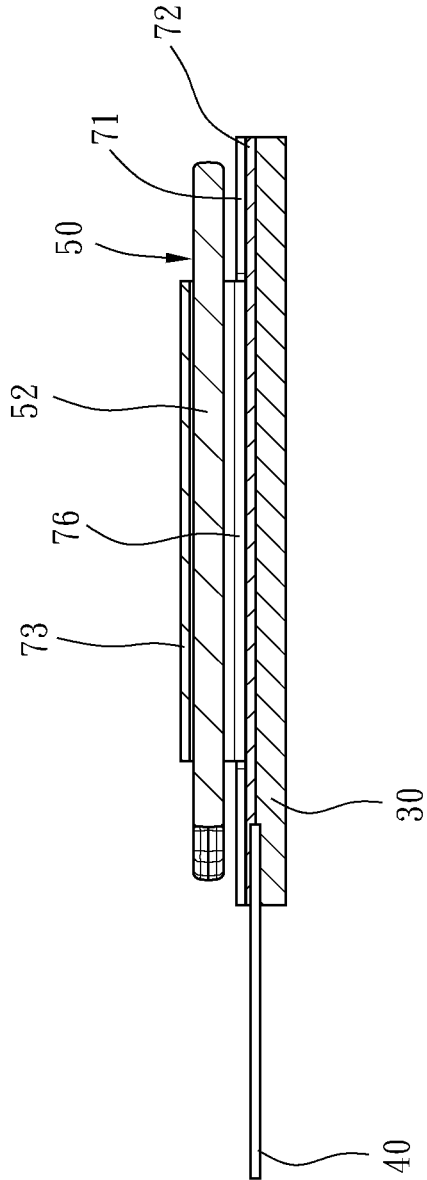
FIG. 11 is a sectional view taken along line 11-11 of FIG. 10.

In this embodiment, the elastic band 70 is a bandage and the positioning cloth 26 is omitted, that is, a through trough 76 is formed only by the bandage. Furthermore, as shown in FIGS. 9 to 11, one end of the elastic band 70 is folded back and fixed by sewing to form an inner layer 71 and an outer layer 72 stacked on the inner layer 71, and the other end of the elastic band 70 is folded back and fixed by sewing to form a tail groove 77 for installation of the bandage fastener 60. The outer layer 72 has a positioning portion 73 provided with two opposite sides 74 thereof sewn to the inner layer 71, such that the through trough 76 is formed between the positioning portion 73 and the inner layer 71, as shown in FIG. 11, and further, the two opposite sides 74 of the positioning portion 73 are engaged with the anchor portion 522 of the pressurized member 50, such that the anchor portion 522 and the positioning portion 73 are interfered with each other to prevent the insertion portion 52 from being easily separated from the through trough 76. In addition, the outer layer 72 further has two notches 75 abutted with two ends of the through trough 76, and one of the notches 75 corresponds to the dressing change indicator label 40. As such, the elastic band 70 and the pressurized member 50 provided in this embodiment can also be assembled with each other in a detachable manner.

As indicated above, the pressurized member 50 provided by the pressurized tourniquet 10, 10' of the present invention is detachably assembled with the elastic band 20, 70 and not fixed to each other by traditional sewing methods. This makes the production process relatively simple and fast. Once the elastic band 20, 70 is too dirty, the hemostatic dressing 30 needs to be replaced, or the pressurized member 50 is damaged, the user simply replaces the damaged accessories without the need to discard the entire set. This can significantly reduce the financial burden for the user.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pressurized tourniquet comprising:
   an elastic band including an inner surface, an outer surface, and a through trough formed at the outer surface and having an extending direction vertical to a longitudinal direction of the elastic band and parallel to a width direction of the elastic band;
   a hemostatic dressing disposed on the inner surface of the elastic band; and
   a pressurized member including a base portion, an insertion portion, and a first pressurized portion, the insertion portion and the first pressurized portion being on the same side of the base portion and each having one end thereof connected with the base portion, the insertion portion being detachably inserted in the through trough of the elastic band and having a free end forming an anchor portion protruding from one end of the through trough and interfered with the through trough, the first pressurized portion and the insertion portion being parallel to and spaced from each other to form a first slot therebetween for passage of the elastic band;
   wherein a free end of the first pressurized portion forms a first limiting hook in the direction of the anchor portion; a first opening communicating with the first slot is formed between the first limiting hook and the anchor portion;
   wherein the pressurized member further includes a second pressurized portion; the second pressurized portion and the first pressurized portion are on the same side of the base portion and each have one end thereof connected with the base portion; the second pressurized portion and the insertion portion are parallel to and spaced from each other to form a second slot therebetween for passage of the elastic band;
   wherein a free end of the second pressurized portion forms a second limiting hook in the direction of the anchor portion; a second opening communicating with the second slot is formed between the second limiting hook and the anchor portion;
   wherein the insertion portion is disposed between the first pressurized portion and the second pressurized portion, and the first pressurized portion and the second pressurized portion are arranged symmetrically with respect to the insertion portion.

2. The pressurized tourniquet as claimed in claim 1, wherein the first pressurized portion has a first inclined surface abutted with the first limiting hook.

3. The pressurized tourniquet as claimed in claim 1, wherein the first pressurized portion has a first inclined surface abutted with the first limiting hook, and the second pressurized portion has a second inclined surface abutted with the second limiting hook.

4. The pressurized tourniquet as claimed in claim 1, wherein the elastic band includes a bandage provided with the inner surface and the outer surface, and a positioning cloth having two opposite sides thereof sewn to the bandage, such that the through trough is formed between the bandage and the positioning cloth; two ends of the anchor portion are engaged with the two opposite sides of the positioning cloth.

5. The pressurized tourniquet as claimed in claim 1, wherein the elastic band is a bandage; one end of the bandage is folded back and fixed by sewing to form an inner layer and an outer layer stacked on the inner layer; the outer layer has a positioning portion provided with two opposite sides thereof sewn to the inner layer, such that the through trough is formed between the positioning portion and the inner layer; two ends of the anchor portion are engaged with the two opposite sides of the positioning portion.

6. The pressurized tourniquet as claimed in claim 5, further comprising a dressing change indicator label disposed between the inner layer and the hemostatic dressing; the positioning portion of the outer layer further has a notch abutted with one end of the through trough and corresponding to the dressing change indicator label.

7. The pressurized tourniquet as claimed in claim 1, wherein the hemostatic dressing is adhered to the inner surface of the elastic band by using a back adhesive.

\* \* \* \* \*